United States Patent [19]

Lolk

[11] 4,144,752
[45] Mar. 20, 1979

[54] ULTRASONICALLY OPERATIVE DEVICE FOR DETERMINING PHYSICAL QUANTITIES OF A MEDIUM

[75] Inventor: Søren Lolk, Sonderborg, Denmark
[73] Assignee: Danfoss A/S, Nordborg, Denmark
[21] Appl. No.: 843,407
[22] Filed: Oct. 19, 1977
[30] Foreign Application Priority Data
Oct. 27, 1976 [DE] Fed. Rep. of Germany ....... 2648718
[51] Int. Cl.² .............................................. G01F 1/66
[52] U.S. Cl. .................................................. 73/194 A
[58] Field of Search .............................. 73/194 A, 597
[56] References Cited
U.S. PATENT DOCUMENTS 3,751,979  8/1973  Ims ................................... 73/194 A
3,817,098  6/1974  Brown .............................. 73/194 A
4,003,252  1/1977  Dewath ........................... 73/194 A Primary Examiner—Charles A. Ruehl
Attorney, Agent, or Firm—Wayne B. Easton

[57] ABSTRACT

The invention relates to an ultrasonically operative device operable with an ultrasonic signal having a predetermined wave length for measuring physical quantities such as the flow speed of a medium such as water. The device includes an ultrasonic transmitter and an ultrasonic receiver with a tube unit therebetween defining a transmission path for the medium. The tube unit has an internal diameter less than about fifteen times the wavelength of the signal. The tube unit includes an outer metal tube and an inner plastics liner of a plastic such as a polyamide.

5 Claims, 1 Drawing Figure

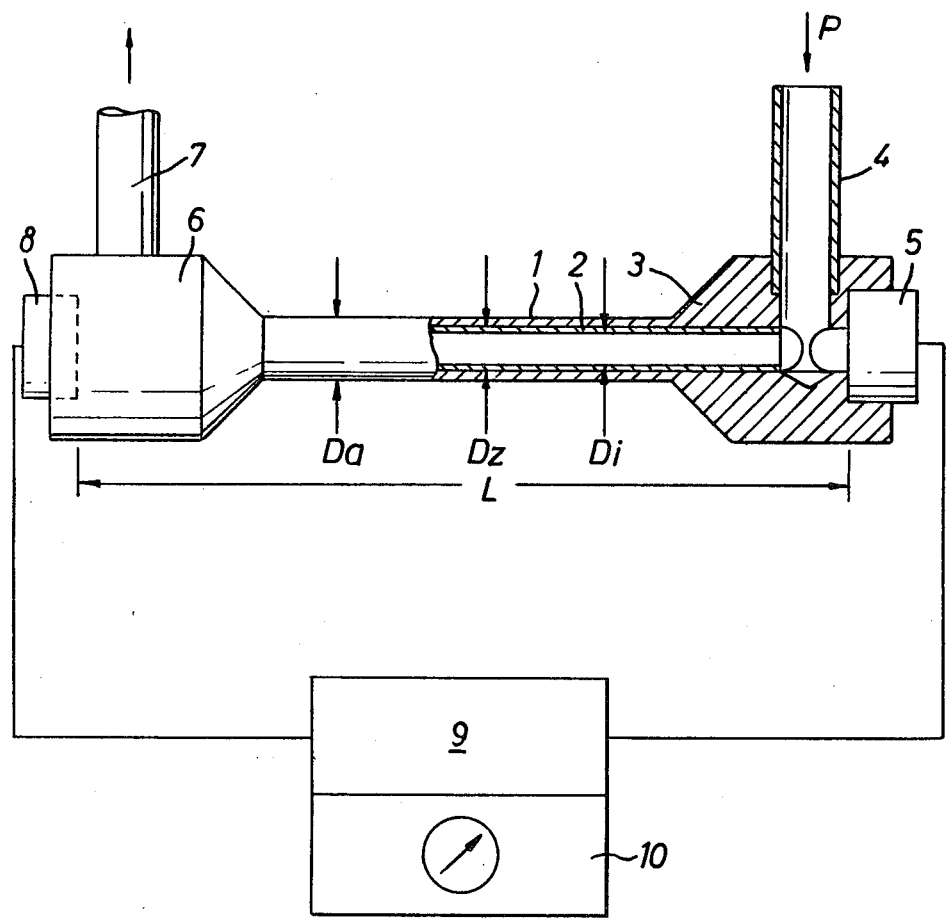

ULTRASONICALLY OPERATIVE DEVICE FOR DETERMINING PHYSICAL QUANTITIES OF A MEDIUM

The invention relates to an ultrasonically operative device for determining physical quantities, particularly the flow speed, of a medium, comprising an ultrasonic transmitter and an ultrasonic receiver which define a transmission path extending along the axis of the measuring tube.

In a known device of this kind, the measuring tube extends between two tubular arcs, the transmitter and receiver each being disposed in the outer wall of one arc. However, one more frequently encounters devices in which the transmitter and receiver are axially displaced and disposed on opposite sides of the measuring tube wall. Further, a device is known in which the measuring tube consists of plastics material and the transmitter and receiver are so mounted on the wall of the measuring tube that a transmission path of zig-zag shape is obtained in which the ultrasonic waves are reflected several times at the wall of the measuring tube.

In operation, the transmitter is excited by a pulse so that it gives off an ultrasonic signal for a short period. The time taken for the ultrasonic signal to reach the receiver is found. If in the case of a fluent medium the period is measured in the direction of flow as well as against the direction of flow, the speed of flow of the medium or its density can be determined. What is important is the accurate determination of the period of the ultrasonic signal. A prerequisite for this is that the incidents of the wave front on the receiver can be very accurately found.

It has been found that the time measurements become all the more inaccurate, the less is the width, i.e. the diameter in the case of a circular cross-section, of the measuring tube. However, there is an intense desire to have measuring tubes of small cross-section, for example if small amounts of the medium are to be passed through with a comparatively large speed of flow.

The invention is therefore based on the problem of providing a device of the aforementioned kind in which one can work with very small tube sections and nevertheless permit an accurate measurement of the period.

This problem is solved according to the invention in that the measuring tube has an internal width of less than about 15 times the wave length of the ultrasonic signal and that the inner surface of the measuring tube consists of a material having a lower acoustic impedance than metal.

This construction is based on the surprising discovery that in measuring tubes of small cross-section an accurate measurement of the period fails because of the fact that the receiver is impinged by preceding waves of not inconsiderable energy even before the arrival of the wave front formed by the fundamental wave. It was found that these preceding waves are waves of a first and second kind radiated from the transmitter crystal and, by reason of the wave equation, being propagated through the medium at a higher speed than the planar fundamental wave. According to the invention, the fact is utilised that these waves of the first and second kind possess a propagation direction that is at an angle to the propagation direction of the fundamental wave. If the fundamental wave is radiated in the direction of the axis of the measuring tube, it reaches the receiver undamped whereas the waves of the first and second kind strike the tube wall and are reflected therefrom but are damped in the process because of the lower acoustic impedance at the inner surface. This ensures that the preceding waves are so weak that the receiver cannot yet be excited thereby.

With most fluids, the speed of sound lies between 1500 and 1800 m/s. For water it is 1500 m/s. The ultrasonic frequency should be selected to be as high as possible so that there is the best possible power of resolution; however, an excessively high frequency gives excessively large transmission losses. A favourable value for the ultrasonic frequency is near 1 MHz. At this frequency, the upper width of a measuring tube intended for water is between 20 and 25 mm. By means of measurements, one can show that with a measuring tube of metal no problems are encountered with preceding waves in the case of a diameter of 25 mm, whereas these problems arise markedly when the diameter falls below 20 mm. For other fluids and other ultrasonic frequencies, corresponding considerations apply.

The length of the transmission path must not fall below a particular minimum size for the devices here considered because with excessively small spacings between the converters the time difference for the sound measurement becomes too small and no accurate measuring result can be obtained. This lower limit is solely a practical value depending on the device and the measuring technique; it generally amounts to at least 40 to 50 times the wave length of the ultrasonic signal. However, longer transmission paths are often used, e.g. from 150 to 200 times the wave length, for example when the crystal of the ultrasonic transmitter has a smaller cross-section than the measuring tube cross-section and this tube section is to be completely filled with a sound wave in order to obtain a mean value. However, transmission paths of 300 to 500 times the wave length are not unusual. In all cases, one obtains the reflections with damping of the waves of the first and second kind in accordance with the invention. Frequent reflections lead to correspondingly greater damping.

In particular, the inner surface of the measuring tube may be of plastics material, preferably polyamide. Plastics materials either inherently have a considerably lower acoustic impedance than metal or can be manufactured with such an impedance without difficulty.

It is sufficient if merely an inner wall lining consists of plastics material. The measuring tube can therefore be made from metal. This is often desirable where higher requirements are placed on the strength or temperature resistance of the measuring tube.

It has been found that to obtain the desired results it is sufficient to have comparatively small thicknesses for the wall lining. The thickness need merely be 0.5 to 1.5 mm, preferably about 1 mm.

The invention will now be described in more detail with reference to an example illustrated in the drawing which diagrammatically shows a part-section of a device according to the invention.

A measuring tube 1 is provided with an internal wall lining 2 of polyamide. At one end, the measuring tube has a head 3 which receives a supply tube 4 and in an axial extension of the measuring tube 1 an ultrasonic converter 5. At the other end there is a head 6 receiving a supply tube 7 and in an axial extension of the measuring tube 1 a second ultrasonic converter 8.

The two converters 5 and 8 are connected to a control and measuring circuit 9. In a first cycle, this gives an exciter impulse to the converter 5, whereupon the latter produces an ultrasonic signal as a transmitter. The ultrasonic signal received by the converter 8 as the receiver is notified to the circuit 9 so that the latter can determine the period of the ultrasonic signal. Since the medium is supplied in the direction of the arrow P, this measurement of the period occurs in the direction of flow. During the second cycle, the control and measuring circuit 9 gives an exciter pulse to the converter 8 so that this serves as the transmitter for the next ultrasonic signal. The ultrasonic signal received by the converter 5 that now acts as the receiver is notified to the circuit 9 so that this time the period is measured against the direction of flow. From these measuring results, an evaluating circuit 10 connected to the circuit 9 determines and indicates the flow speed and, since the tube cross-section is given, also the quantity that is flowing through. The determined values also permit the speed of sound in the medium and thus its density to be determined.

In the present example, the medium is water at which the speed of sound is about 1500 m/s. The ultrasonic converters work with a fundamental frequency of 1 MHz. The wave length of an ultrasonic oscillation therefore amounts to 1.5 mm. The measuring tube has an external diameter $D_a$ of 20 mm, a wall thickness of 1 mm, so that an intermediate diameter $D_z$ of 18 mm is obtained.

The plastics lining 2 likewise has a wall thickness of 1 mm, thereby resulting in an internal diameter $D_i$ of 16 mm. This substantially corresponds to 11 times the wavelength. The length of the transmission path L is 50 cm. This corresponds to 333 times the wave length. With this construction, the waves preceding the actual wave front are negligibly small. If, on the other hand, one uses a measuring tube having the same internal diameter and that is made from steel, one obtains very marked preceding waves.

Similar good results were also achieved with plastics linings of 0.5 and 2.0 mm. The same applies to smaller internal diameters, for example 10 or 14 mm, as well as somewhat larger internal diameters, for example 20 mm, and to different lengths L, for example 20 cm or 75 cm.

I claim:

1. An ultrasonically operative device operable with an ultrasonic signal having a predetermined wave length for determining physical quantities such as the flow speed of a medium, comprising, an ultrasonic transmitter and an ultrasonic receiver, tube means defining a transmission path extending between said transmitter and said receiver, said tube means having an internal diameter of less than about 15 times said predetermined wave length, said tube means having an inner surface of a material having a lower acoustic impedance than metal.

2. A device according to claim 1 wherein said material is a plastic.

3. A device according to claim 2 wherein said tube means comprises an outer metal tube and an inner plastic liner.

4. A device according to claim 3 wherein the thickness of said plastic liner is 0.5 to 1.5 mm.

5. A device according to claim 2 wherein said plastic is a polyamide.

* * * * *